United States Patent [19]

Kurihara-Bergstrom et al.

[11] Patent Number: 5,374,645

[45] Date of Patent: Dec. 20, 1994

[54] TRANSDERMAL ADMINISTATION OF IONIC PHARMACEUTICALLY ACTIVE AGENTS VIA AQUEOUS ISOPROPANOL

[75] Inventors: Tamie Kurihara-Bergstrom, New City, N.Y.; Puchun Liu, Storrs, Conn.

[73] Assignee: Ciba-Geigy Corporation, Ardsley, N.Y.

[21] Appl. No.: 17,364

[22] Filed: Feb. 11, 1993

Related U.S. Application Data

[63] Continuation of Ser. No. 788,895, Nov. 7, 1991, abandoned, which is a continuation of Ser. No. 468,387, Jan. 22, 1990, abandoned.

[51] Int. Cl.$^5$ ............................................. A61K 31/485
[52] U.S. Cl. .................................... 514/282; 514/411; 514/567; 514/570; 514/653; 514/947
[58] Field of Search ............... 514/653, 282, 411, 567, 514/570, 947

[56] References Cited

U.S. PATENT DOCUMENTS 3,551,554 12/1970 Herschler ................................. 424/7
5,064,654 11/1991 Berner et al. ........................ 424/448
5,073,539 12/1991 Mazzenga et al. .

FOREIGN PATENT DOCUMENTS 0267617 5/1988 European Pat. Off. .
1504302 3/1978 United Kingdom .

OTHER PUBLICATIONS

Friend et al–Journal of Controlled Release, 7 (1988) 243–250.
Chemical Abstracts 11th Coll. Index, vol. 96–105, pp. 8700–8702 Cs, 1982–1986.

Primary Examiner—Marianne M. Cintins
Assistant Examiner—William R. A. Jarvis
Attorney, Agent, or Firm—Irving M. Fishman; Karen G. Kaiser

[57] ABSTRACT

A composition for the transdermal administration of ionic pharmaceutically active agents comprising the active agent along with a suitable counter ion, water, and isopropanol, at an adjusted pH is disclosed. Also disclosed are transdermal systems which employ this composition and methods of transdermally administering such agents therewith. The main advantage achieved is improved flux rates of active agent over other systems.

6 Claims, 1 Drawing Sheet

TRANSDERMAL ADMINISTATION OF IONIC PHARMACEUTICALLY ACTIVE AGENTS VIA AQUEOUS ISOPROPANOL

This application is a continuation of application Ser. No. 07/788,895, filed Nov. 7, 1991, now abandoned, which is a continuation of Ser. No. 468,387 filed Jan. 22, 1990 now abandoned.

FIELD OF THE INVENTION

The present invention relates to the area of pharmaceutically active ionic drugs and their administration transdermally. It also relates to flux enhancement methods and materials.

BACKGROUND OF THE INVENTION

The advantages of transdermal administration of pharmaceutically active agents over other routes is well documented. Among these advantages are: avoidance of gastric irritation, elimination of side effects, evading the problem of hepatic first-pass metabolism, reduction of risks associated with parenteral treatment, delivery of the active agent directly to the bloodstream, and others.

The primary limitation to the widespread use of the transdermal route however is the barrier properties of skin. Many substances do not have the capability of migrating across intact skin. This, of course, is not all that surprising in that one of the skin's primary function is to act as a barrier.

In compact skin, the stratum corneum is quite impermeable, a property conferred primarily from its lipid character. However, both lipoidal and pore pathways do exist in and through the stratum corneum. These pathways are exploited for the transdermal administration of the known transdermally administrable drugs, and as such, the hydrophobic/hydrophilic character of the drug being administered becomes of great importance. The stratum corneum is considered overall to be hydrophobic in nature and substantial resistance is encountered when hydrophilic/ionized molecules attempt to cross it.

One approach to solving the low permeation difficulties is the use of permeation enhancers, materials which increase the flux of the desired agent through the skin. Permeation enhancers can react with either skin components or with the desired agent. In either event the flux of the desired agent is enhanced over that which would be achieved in the absence of the permeation enhancer.

A wide range of enhancers have been proposed, heretofore. Representative disclosures of permeation enhancers in the an include the following: cyclic urea compounds (U.S. Pat. No. 4,677,131), a monovalent alcohol ester (U.S. Pat. No. 4,605,670), dimethyl sulfoxide (U.S. Pat. No. 3,551,554), hydrocarbons, ketones, esters, ethers, alcohols, amines, or sulfones (British Patent 1,504,302), a partial glyceride of a medium chain length fatty acid (U.S. Pat. No. 4,202,888), lower alkyl amides (U.S. Pat. No. 3,472,931), 2-pyrrolidone or N-lower alkyl-2-pyrrolidone (U.S. Pat. No. 4,132,781), $C_3$-$C_4$ diols (U.S. Pat. No. 4,557,943), sugar ester+a sulfoxide or phosphine oxide (U.S. Pat. Nos. 4,130,667, 3,952,099 and 4,046,886), higher alcohols+esters (U.S. Pat. No.4,299,826), ethanol+azone or oleic acid (Eur. Pat. EP 271,983), amines (Jpn Kokai Tokyo Koho JP 62,240,628), oleic acid+2 ethyl- 1,3 hexanediol, ethanol+glycerol monolaurate (U.S. Pat. No. 4,764,379).

Based on these and other references, it is clear that little or no attention has been given to the problem of reducing permeation enhancer induced skin irritation, to the manipulation of active agents per se so as to enhance skin permeation, to drags which permeate the stratum corneum to a significant extent by routes other than the lipoidal pathway, to the implication that particular enhancers often only work with particular active agents.

Several references mentioning isopropanol mixed with other solvents as percutaneous absorption enhancers include THERATECH INC., "Topical pharmaceutical composition with improved skin penetration—containing alkanol and compound, e.g. oleic acid", (EP 267,617, JP 63,211,241), PROCTER AND GAMBLE CO., "Topical composition containing lipophilic pharmaceutical with diol and myristate or laurate ester vehicle for enhanced penetration", (EP 43,738, JP 57,081,408, ZA 8,140,650, CA 1,165,240, DE 3,172,516), Friend et at., "Transdermal delivery of levonorgestral I: alkanols as penetration enhancers in vitro." (J. Control. Rel. 3 (1988) pp. 243–250).

Many pharmaceutically active agents an weak organic acids or bases having the potential to ionize in the physiologic pH range, The extreme hydrophilic character of ionic drugs severely limits their penetration through the lipophilic heterogeneous stratum corneum so that for all practical purposes only the unionized form can pass through the barrier.

OBJECTS OF THE INVENTION

Therefore, it is an object of the present invention to provide an ionic drug permeation enhancer capable of increasing the permeation of the ionic species.

It is another object of this invention to provide a single family of permeation enhancer systems applicable to broad number of structurally dissimilar drugs.

Yet another object is to provide a permeation enhancer which is non-irritating to the skin.

SUMMARY OF THE INVENTION

These and other objects of the invention are surprisingly realized by a transdermal system comprising a pharmaceutically acceptable active agent having an ionic species, a counterion for the ionic species of the agent, water, and isopropanol, the composition maintained in a pH range of from about 3.0 to about 8.5.

DETAILED DESCRIPTION OF THE INVENTION

Figure 1:
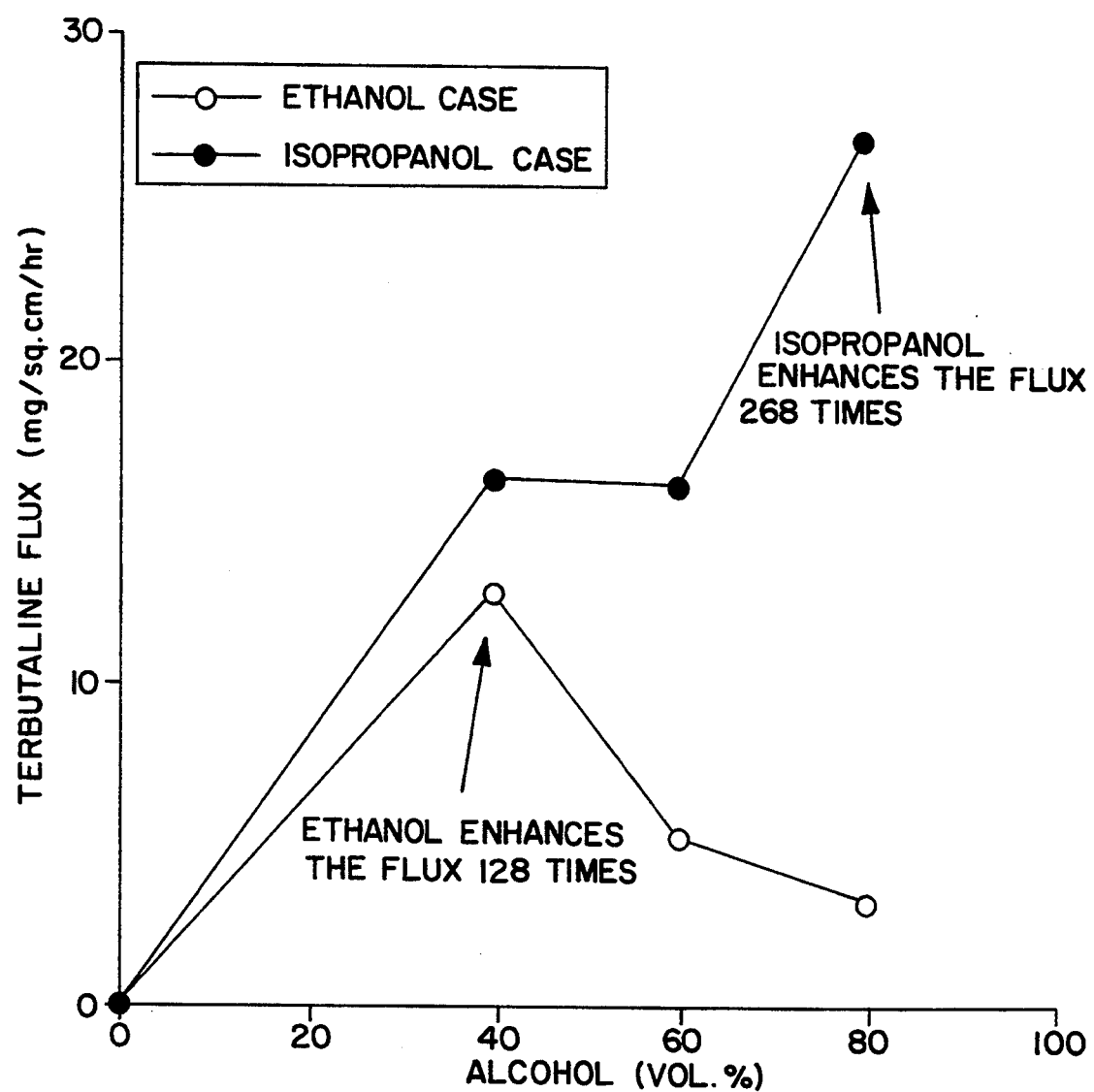
FIG. 1 is a plot of the flux of terbutaline against the volume % of alcohol, ethanol and isopropanol, the raw data of which is found in Table 1 of Example 1.

The instant invention is a composition for transdermal administration comprising a pharmaceutically acceptable active agent maintained at a pH at which a significant portion thereof is in an ionic form, water, and isopropanol. This composition allows for the enhanced transdermal administration of ionic and zwitterionic species without skin irritation. The use of the pH controlled aqueous isopropanol counterion composition is especially useful for improving the flux of drugs, especially hydrophilic drugs, since it combines increasing the lipophilic character of the drug in question and reducing the strateum corneum barrier.

More specifically, the invention composition contains:
1. a pharmaceutically acceptable agent in a pharmacologically effective mount,
2. a pH maintained in the range of 3.0 to 8.5 such that a substantial portion of the active agent species is maintained in an ionic state,
3. a pharmaceutically acceptable counter-ion,
4. isopropanol, and
5. water.

The pharmaceutically acceptable agent administrable via this invention is not limited to any class of therapeutic agent. However, it is particularly useful for the administration of agents having an ionic species in the transdermally acceptable pH range. This includes a wide range of weakly acidic and weakly basic subpstances.

Specific drugs for which the instant invention is suitable include, but is not limited to: amantadine, arecoline, atropine, bromocriptine, buprenorphine, caffeine, chlorpromazine, chloroquine, cimetidine, diclofenac, diazepam, dobutamine, dopamine, epinephrine, fenoprofen, fentanyl, fluphenazine, flurazepam, formoterel, imipramine, indomethacin, isoniazid, isoproterenol, levorphanol, lidocaine, methylphenidate, mecamylamine, meperidine, minoxidil, morphine, nicomorphine, nicotine, nefedipine, pindolol, prinomide, propanolol, promethazine, physostigmine, rifampin, salbutamol, salicylic acid, sufentanyl, terbutaline, theophylline, timolol, trimipramine, verapamil, CGS 12970, CGS 13080, CGS 15435A, and CGS 16949A.

Especially suitable for administration in the invention manner are: arecoline, terbutaline, buprenophrine, diclofenac, indomethacin, levorphanol, morphine, nicotine, propranolol, and salbutamol.

The invention solvent, aqueous isopropanol, can be used by itself or in conjunction with other solvents. The optional solvents suitable for use in the invention must be non-irritating to the skin, have a low dielectric medium for increasing the active agent's lipophilicity, and be a stratum corneum barrier eliminator. The dual effect on the agent and on the skin results in an overall enhancement of the agent permeation through the skin.

More specifically, the invention composition can increase the formation of ion pairs as well as decrease the disassociation constants of weakly acidic and weakly basic drug substances. This results in an increase in electrical neutrality and lipophilic characteristics of the permeant. In addition, the instant combination can also eliminate a portion of the hydrophobic barrier of the stratum corneum.

The invention compositions contain a pharmaceutically acceptable active agent-counter ion complex in a pharmaceutically acceptable amount, a vehicle comprising isopropanol and water, having about 5% to about 95% isopropanol and a pH in the range of 3.0 to about 8.5.

The counter ion for use in forming the pharmaceutically acceptable active agent-counter ion complex may be organic or inorganic; the only limitation is that the counter ion be pharmaceutically acceptable. For example, these include hydrochloric, hydrobromic, hydroiodic, phosphoric, sulfuric, nitric, sulfamic, citric, lactic, maleic, pyruvic, oxalic, succinic, tartaric, cinnamic, acetic, trifluoroacetic, benzoic, salicylic, gluconic, or ascorbic as the anion and sodium, calcium, and potassium as the cation. The amount of counter-ion is dependent the neutralization of the ionic agent.

The vehicle is 5% to 95% by volume isopropanol in water, preferably 20% to 93%, more preferably 40% to 92%, more preferably about 50% to about 90% by volume isopropanol in water.

The pH range is preferably 3.0 to 8.5, more preferably 4.5 to 8.3, most preferably 5.5 to 8.0. It is preferable to have the pH of the composition beyond 1 pH unit, most preferably 2 pH units, of the $pK_a$, (dissociation constant) of the pharmaceutically acceptable active agent, i.e., more than 2 pH units higher for weak acid and more than 2 pH units lower for weak base.

The composition may also contain other optional components which enhance their cosmetic appeal or acceptability, i.e., thicken, pigments, fragrances, perfumes, and the like. In the case of skin irritation cause by the concentrated agent and its counter-ion, other components which tent to reduced the irritation may be incorporated into the compositions as desired.

In view of this, the invention is not limited to any specific type or class of active permeants provided they meet the above criteria and are capable of ionization. Some routine experimentation or testing may be required to determine optimum conditions such as exact pH, exact isopropanol concentration exact agent concentration, and the concentration ratio of counter-ion to the active agent.

The invention encompasses the use of a broad range of pharmaceutically-active permeants which are capable of ionization. The compositions of this invention may be utilized in delivering active permeants to the "target" areas: (1) for local effects, e.g., at the surface of the skin, in the stratum corneum itself, in the viable epidermis and upper dermis just below the epidermis, and/or in the various glands and structures in and beneath the dermis (e.g., subcutaneous adipose, dermal vasculature) and (2) for system effects, i.e., into the general system.

The pharmaceutically-active permeants may be used in the compositions and methods of the present invention at any safe and effective level. Dosages will obviously be a function of various variables, such as how active the agent is; how it is formulated; if an enhancer is used, how soluble it is in the penetration enhancing vehicle; how often it is to be applied; whether the use is to be topical or systemic; whether two or more active permeants are to be combined; the particular patient being treated; and the like. In any event, the dosage should be the smallest that will achieve the desired result and the period of administration should be as short as possible to attain this result. Hence, the invention is not directed to any particular amount of active ingredients as long as it is safe and effective.

The following non-limiting examples (EXAMPLES 1 AND 2) demonstrate the improvement in penetration of terbutaline with human skin in vitro that is obtained by utilizing the aqueous isopropanol/pH/counter-ion combination. In conducting these tests, human skin consisting of heat-separated back epidermis was placed in a standard vertical or horizontal 2-chamber diffusion cell. A normal saline solution (with 0.01% Gentamicin as the antibiotic) was added to the receiver chamber in contact with the subcutaneous side of the skin, and the test composition, consisting the active weak base and the aqueous alcohol/pH/counter-ion combined formulation, as indicated in each example, was added to the donor chamber. The cell assembly was kept at a constant temperature at about 32° C. The diffusate from the receiver chamber was withdrawn either automatically and continually through a flow-through system or manually by taking sample at predetermined time intervals. The amount of drug in the diffusate was measured using standard analytical techniques. Each test was run using separate skin sample. The results are reported in terms of flux (mcg/cm$^2$/hr).

EXAMPLE 1

This example (TABLE I) shows the improved terbutaline flux utilizing aqueous alcohol/pH/sulfate combination. The various aqueous alcohol includes aqueous ethanol and aqueous isopropanol in the different concentrations. These results are plotted in FIG. 1. While ethanol enhances the terbutaline flux 128 times at around 40% ethanol, isopropanol enhances the terbutaline flux 268 times at around 80% isopropanol. The aqueous isopropanol with its stronger ion-pair medium property and its stronger skin permeation enhancement ability gives much better overall terbutaline flux enhancement than the aqueous ethanol.

TABLE I

Terbutaline Skin Flux in Different Aqueous Alcohol/pH/Sulfate Combinations[a]

| Aq. Alcohol (vol. %) | pH[c] | Terbutaline | Flux[b] |
|---|---|---|---|
| (0%) | 3.8 | 0.1 | (1) |
| ethanol (40%) | 4.6 | 12.8 | (128) |
| ethanol (60%) | 5.0 | 5.3 | (53) |
| ethanol (80%) | 5.8 | 3.3 | (33) |
| isopropanol (40%) | 4.4 | 16.3 | (163) |
| isopropanol (60%) | 4.9 | 16.1 | (161) |
| isopropanol (80%) | 5.8 | 26.8 | (268) |

[a]The counter-ion is sulfate (sulfuric acid) with the terbutaline-to-sulfate mole concentration ratio = 2.
[b]The number in bracket is the relative flux, taking the flux in water case as unity.
[c]The pH's are all more than 2 units lower than pKa (8.7).

EXAMPLE 2

This example (TABLE II) shows the improved terbutaline flux utilizing aqueous ethanol/pH/chloride combination. With chloride as the counter-ion and the unity terbutaline-to-chloride mole concentration ration, the maximum flux enhancement is observed at around 45% ethanol concentration with the flux enhancement factor 50.

TABLE II

Terbutaline Skin Flux in Different Aqueous Ethanol/pH/Chloride Combinations[a]

| Ethanol (Vol. %) | pH[c] | Terbutaline | Flux[b] |
|---|---|---|---|
| 0% | 3.8 | 0.1 | (1) |
| 35% | 4.2 | 4.1 | (40) |
| 45% | 4.0 | 5.0 | (50) |
| 78% | 4.0 | 0.6 | (6) |

[a]The counter-ion is chloride (hydrochloride acid) with the terbutaline-to-chloride mole concentration ratio = 1.
[b]The number in bracket is the relative flux, taking the flux in water case as unity.
[c]The pH's are all more than 2 units lower than pXa (8.7).

EXAMPLE 3

This example (TABLE III) presents the aqueous isopropanol/pH/counter-ion combinations for several pharmaceutical-active agents, including weak bases and weak acids with different pKa values. The aqueous isopropanol concentration, the kind of counter-ion, and the mixture pH are optimistically selected according to this invention.

TABLE III

Aqueous Isopropanol/pH/Counter-Ion Combined Systems for Several Pharmaceutical-Active Agents

| Agents | pKa | Optimun pH | Optimun Isopropanol Concentration | Optimun Counter-ion |
|---|---|---|---|---|
| Weak Base | | | | |
| Propanolol | 9.5 | 4.0–7.5 | 75–85% | Chloride |
| Salbutamol | 8.7 | 4.0–6.7 | 75–85% | Sulfate |
| Morphine | 8.2 | 4.0–6.2 | 75–85% | Sulfate |
| Physostigmine | 6.1 | 4.0–4.1 | 75–85% | Sulfate |
| Weak Acid | | | | |
| Salicylic Acid | 4.2 | 6.2–8.0 | 75–85% | Sodium |
| Indomethacin | 4.5 | 6.5–8.0 | 75–85% | Sodium |
| Fenoprofen | 4.5 | 6.5–8.0 | 75–85% | Calcium |
| Diclofenac | 4.7 | 6.7–8.0 | 75–85% | Sodium |

EXAMPLE 4

This example (TABLE IV) shows the test results of primary skin irritation with various concentrations of isopropanol (pH range 5-b). The primary skin irritancy of pure isopropanol and 60% isopropanol were evaluated in compliance with the conditions specified in the regulation for the enforcement of the Federal Hazardous Substance ACT (16 CFR 1500). Based on erythema and edema, the Primary irritation Index (P11) was found to be 2.5 and 2.4 for pure isopropanol and for 60% isopropanol, respectively. No changes in the coloration or texture of the skin and corrosion (necrosis) were noted in response to either test material. In summary, neither pure isopropanol nor aqueous isopropanol are classified as primary irritants or as corrosives by dermal application.

TABLE IV

Primary Skin Irritation Tests of Aqueous Isopropanol in Rabbits

| Isopropanol (vol. %) | Primary Irritation Index (P11)[a] |
|---|---|
| 60% | 2.4 |
| 100% | 2.5 |

[a]A primary irritant is one which gives a P11 of 5 or more on scale of 0–8.

While the above examples illustrate numerous embodiments of the invention, the scope of the invention is limited only by the operability of the ionic agents in the aqueous isopropanol/pH/counter-ion combined medium. It is to these combinations and the unexpected property of enhanced skin penetration of the ionic agents possessed by these combinations that the present invention is drawn. It is, therefore, limited in scope only by the appended claims and their functional equivalents.

We claim:

1. A composition for the transdermal administration of a pharmaceutically acceptable ionic salt of a pharmaceutically active weak acid or weak base comprising a pharmaceutically effective amount of said ionic salt of said pharmaceutically active weak acid or weak base and about 60% to 80% isopropanol in water having a pH of about 3.0 to about 8.5.

2. A composition for the transdermal administration of a pharmaceutically acceptable ionic salt of a pharmaceutically active weak acid or weak base comprising a pharmaceutically effective amount of said ionic salt of said pharmaceutically active weak acid or weak base and about 60% to 80% isopropanol in water having a pH of about 4.5 to about 8.3.

3. The composition of claim 2 wherein said pH range is about 5.5 to about 8.0.

4. A composition for the transdermal administration of a pharmaceutically acceptable ionic salt of a pharmaceutically active weak acid or weak base comprising a pharmaceutically effective amount of said ionic salt of said pharmaceutically active weak acid or weak base and about 60% to 80% isopropanol in water having a pH of about 3.5 to about 8.5, wherein said pharmaceutically active weak acid or weak base is selected from salbutamol, physostigmine, buprenorphine, morphine, diclofenac, and fenoprofen.

5. A composition for the transdermal administration of a pharmaceutically acceptable ionic salt of a pharmaceutically active weak acid or weak base comprising a pharmaceutically effective amount of said ionic salt of said pharmaceutically active weak acid or weak base and about 60% to 80% isopropanol in water having a pH of about 3.5 to about 8.5, wherein said ionic salt of said weak acid is selected from sodium, calcium, and potassium salts of said weak acid and said ionic salt of said weak base is selected from the hydrochloric, hydrobromic, hydroiodic, phosphoric, sulfuric, nitric, sulfonic, citric, lactic, maleic, pyruvic, oxalic, succinic, tartaric, cinnamic, acetic, trifluoroacetic, benzoic, salicylic, gluconic, and ascorbic acid salts of said weak base.

6. A method of administering a pharmaceutically acceptable ionic salt of a pharmaceutically active weak acid or weak base, having an enhanced transdermal flux rate, to a subject comprising applying a pharmaceutically effective mount of a transdermal composition of a pharmaceutically acceptable ionic salt of a pharmaceutically active weak acid or weak base to the skin of said subject, said composition comprising a pharmaceutically effective amount of said ionic salt of said pharmaceutically active weak acid or weak base and about 60% to 80% isopropanol in water having a pH of about 3.5 to about 8.5.

* * * * *

UNITED STATES PATENT AND TRADEMARK OFFICE
CERTIFICATE OF CORRECTION

PATENT NO. : 5,374,645
DATED : December 20, 1994
INVENTOR(S) : Kurihara-Bergstrom, et al.

It is certified that error appears in the above-indentified patent and that said Letters Patent is hereby corrected as shown below:

Column 6, line 59, after "ph of about" delete "3.0" and insert --3.5--.

Signed and Sealed this

Twenty-eight Day of March, 1995

Attest:

BRUCE LEHMAN

Attesting Officer     Commissioner of Patents and Trademarks